US012658316B2

(12) United States Patent
Bradley et al.

(10) Patent No.: US 12,658,316 B2
(45) Date of Patent: *Jun. 16, 2026

(54) METHOD AND APPARATUS FOR ACQUIRING INFORMATION

(71) Applicant: EOS Technology Holdings Inc., New York, NY (US)

(72) Inventors: Nathaniel T. Bradley, Tucson, AZ (US); David Bradley, Tucson, AZ (US); Edward William Withrow, III, Malibu, CA (US)

(73) Assignee: EOS Technology Holdings Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/774,639

(22) Filed: Jul. 16, 2024

(65) Prior Publication Data

US 2024/0371515 A1 Nov. 7, 2024

Related U.S. Application Data

(63) Continuation of application No. 17/892,524, filed on Aug. 22, 2022, now Pat. No. 12,040,088, which is a
(Continued)

(51) Int. Cl.
| | |
|---|---|
| *G16H 20/30* | (2018.01) |
| *G06V 40/10* | (2022.01) |
| *G06V 40/16* | (2022.01) |
| *G06V 40/70* | (2022.01) |
| *G16H 40/67* | (2018.01) |
(Continued)

(52) U.S. Cl.
CPC ............. *G16H 40/67* (2018.01); *G06V 40/10* (2022.01); *G06V 40/161* (2022.01); *G06V 40/70* (2022.01); *G16H 20/30* (2018.01); *H04L 63/0861* (2013.01); *G06V 40/179* (2022.01); *G06V 2201/10* (2022.01); *G16H 10/20* (2018.01); *G16H 10/60* (2018.01); *G16H 20/10* (2018.01); *G16H 50/30* (2018.01); *H04L 63/0428* (2013.01)

(58) Field of Classification Search
None
See application file for complete search history.

(56) References Cited

U.S. PATENT DOCUMENTS

| | | | |
|---|---|---|---|
| 4,237,344 A | 12/1980 | Moore | |
| 5,377,258 A | 12/1994 | Bro | |
(Continued)

FOREIGN PATENT DOCUMENTS

| | | | | |
|---|---|---|---|---|
| CN | 107316222 A | 11/2017 | | |
| WO | 2012156374 A1 | 11/2012 | | |
| WO | WO 2012/0156374 | * 11/2012 | ............. | G06F 19/00 |

*Primary Examiner* — John A Pauls
(74) *Attorney, Agent, or Firm* — Goodhue, Coleman & Owens, P.C.

(57) ABSTRACT

A system, device, and method for acquiring information. An image and metadata associated with the image are captured utilizing a wireless device. The image and the metadata are associated with a device incapable of communication with an external device. Information associated with the device and user information is determined. The user information is characterized in context of historical data for at least the user and other similar users. The information is distributed from the wireless device to one or more authorized devices.

20 Claims, 8 Drawing Sheets

Related U.S. Application Data continuation of application No. 15/876,815, filed on Jan. 22, 2018, now Pat. No. 11,437,139, which is a continuation-in-part of application No. 14/979,742, filed on Dec. 28, 2015, now Pat. No. 11,593,764.

(51) Int. Cl.

| | | |
|---|---|---|
| *H04L 9/40* | (2022.01) |
| *G16H 10/20* | (2018.01) |
| *G16H 10/60* | (2018.01) |
| *G16H 20/10* | (2018.01) |
| *G16H 50/30* | (2018.01) |

(56) References Cited

U.S. PATENT DOCUMENTS

| | | | |
|---|---|---|---|
| 6,173,212 B1 | 1/2001 | Valerino | |
| 6,898,299 B1 | 5/2005 | Brooks | |
| 2001/0049321 A1* | 12/2001 | Cohen | A63B 24/00 |
| | | | 482/8 |
| 2002/0045519 A1* | 4/2002 | Watterson | A63B 22/0023 |
| | | | 482/54 |
| 2002/0048600 A1 | 4/2002 | Bhatt et al. | |
| 2002/0082142 A1* | 6/2002 | Cannon | A63B 71/0697 |
| | | | 482/1 |
| 2003/0004758 A1 | 1/2003 | Luttrell | |
| 2004/0030581 A1 | 2/2004 | Leven | |
| 2004/0162702 A1* | 8/2004 | Pandipati | G01G 19/4146 |
| | | | 702/173 |
| 2007/0201727 A1* | 8/2007 | Birrell | A63B 71/0697 |
| | | | 340/5.53 |
| 2007/0232450 A1* | 10/2007 | Hanoun | A63B 71/0622 |
| | | | 482/1 |
| 2008/0207335 A1 | 8/2008 | DiMichele | |
| 2008/0215627 A1 | 9/2008 | Higgins et al. | |
| 2009/0048872 A1 | 2/2009 | Toy et al. | |
| 2009/0197739 A1* | 8/2009 | Hashimoto | A61H 1/001 |
| | | | 482/8 |
| 2009/0326339 A1 | 12/2009 | Horvitz | |
| 2010/0013597 A1 | 1/2010 | Determan et al. | |
| 2010/0079046 A1 | 4/2010 | Vint | |
| 2010/0100226 A1 | 4/2010 | Valerino | |
| 2010/0120585 A1* | 5/2010 | Quy | A61B 5/6838 |
| | | | 482/8 |
| 2011/0092825 A1 | 4/2011 | Gopinathan et al. | |
| 2011/0267459 A1* | 11/2011 | Choi | G06V 30/142 |
| | | | 348/135 |
| 2011/0295613 A1 | 12/2011 | Coyne | |
| 2012/0117232 A1* | 5/2012 | Brown | G06Q 10/10 |
| | | | 709/224 |
| 2012/0209421 A1 | 8/2012 | Valerino | |
| 2012/0296455 A1* | 11/2012 | Ohnemus | G16H 10/60 |
| | | | 700/91 |
| 2013/0129217 A1* | 5/2013 | Gupta | G06V 20/62 |
| | | | 382/182 |
| 2013/0151267 A1 | 6/2013 | Mehdizadeh | |
| 2013/0196822 A1* | 8/2013 | Watterson | A63B 71/0622 |
| | | | 482/9 |
| 2013/0267385 A1* | 10/2013 | Watterson | A63B 24/0062 |
| | | | 482/8 |
| 2014/0046690 A1 | 2/2014 | Gunderson et al. | |
| 2014/0352580 A1 | 12/2014 | Stradiota | |
| 2014/0375470 A1 | 12/2014 | Malveaux | |
| 2015/0048102 A1 | 2/2015 | Dickie et al. | |
| 2015/0120094 A1 | 4/2015 | Kimchi | |
| 2015/0335950 A1* | 11/2015 | Eder | A63B 22/0605 |
| | | | 482/8 |
| 2016/0140496 A1 | 5/2016 | Simms | |
| 2016/0159496 A1 | 6/2016 | O'Toole | |
| 2016/0162660 A1 | 6/2016 | Strong | |
| 2016/0185466 A1 | 6/2016 | Dreano, Jr. | |
| 2016/0257426 A1 | 9/2016 | Mozer | |
| 2016/0321847 A1 | 11/2016 | Briskey | |
| 2016/0361032 A1* | 12/2016 | Carter | G08B 21/0453 |
| 2016/0378921 A1* | 12/2016 | Ohnemus | G16H 20/30 |
| | | | 705/2 |
| 2017/0010665 A1 | 1/2017 | Tanaka et al. | |
| 2017/0132393 A1 | 5/2017 | Natarajan et al. | |
| 2017/0304679 A1* | 10/2017 | Orfield | A63B 21/0724 |

* cited by examiner

802  OBSERVE BIOMETRICS OF A USER

804  ASK USER ABOUT HER CONDITION

806  RECEIVE ANSWERS TO QUESTION(S)

808  BIOMETRICS AND ANSWERS SATISFACTORY?

810  SEND ALERT INCLUDING RELEVANT INFORMATION TO DESIGNATED PARTIES

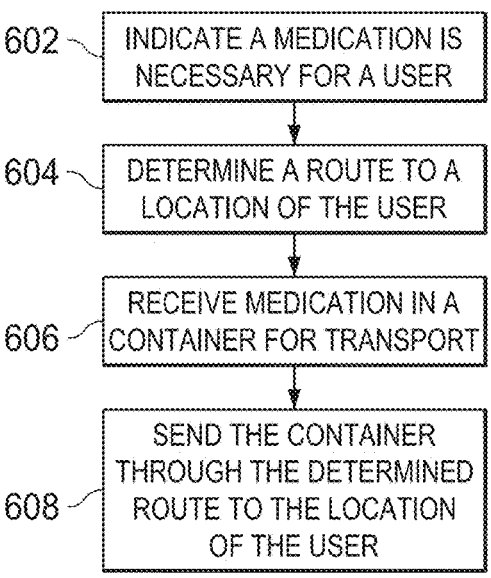

602 — INDICATE A MEDICATION IS NECESSARY FOR A USER

604 — DETERMINE A ROUTE TO A LOCATION OF THE USER

606 — RECEIVE MEDICATION IN A CONTAINER FOR TRANSPORT

608 — SEND THE CONTAINER THROUGH THE DETERMINED ROUTE TO THE LOCATION OF THE USER

FIG. 6

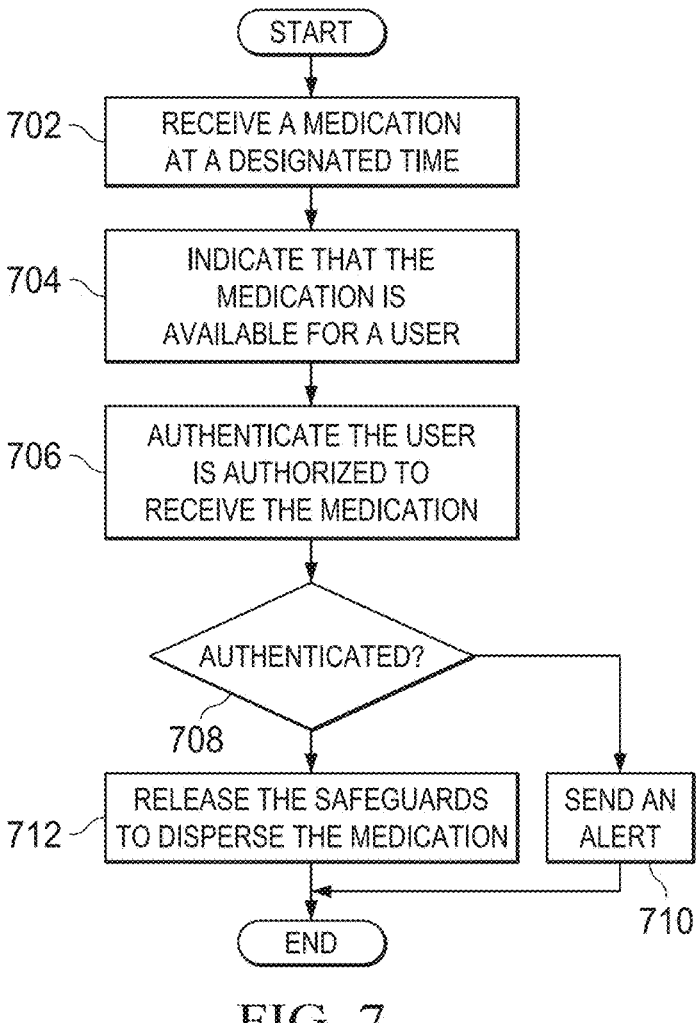

START

702 — RECEIVE A MEDICATION AT A DESIGNATED TIME

704 — INDICATE THAT THE MEDICATION IS AVAILABLE FOR A USER

706 — AUTHENTICATE THE USER IS AUTHORIZED TO RECEIVE THE MEDICATION

708 — AUTHENTICATED?

712 — RELEASE THE SAFEGUARDS TO DISPERSE THE MEDICATION

SEND AN ALERT — 710

END

FIG. 7

IDENTIFY A USER ⟋ 902

CAPTURE AN IMAGE AND METADATA ⟋ 904

PROCESS THE IMAGE AND METADATA
TO DETERMINE USER INFORMATION ⟋ 906

DISTRIBUTE THE USER INFORMATION ⟋ 908

SECURE THE DATA ~1102

SEND THE DATA TO ONE OR MORE
AUTHORIZED DEVICES ~1104

METHOD AND APPARATUS FOR ACQUIRING INFORMATION

PRIORITY

This application is a continuation of U.S. patent application Ser. No. 17/892,524 now U.S. Pat. No. 12,040,088, entitled METHOD AND APPARATUS FOR DETERMINING USER INFORMATION, filed on Aug. 22, 2022 which is a continuation of U.S. patent application Ser. No. 15/876, 815 now U.S. Pat. No. 11,437,139, entitled Method and Apparatus for Biometric Data Collection Combining Visual Data with Historical Health Records Metadata, filed on Jan. 22, 2018 which is a continuation-in-part of U.S. patent application Ser. No. 14/979,742 now U.S. Pat. No. 11,593, 764, entitled Remote User Monitoring System, filed Dec. 28, 2015, the entirety of which is incorporated by reference herein.

BACKGROUND

In recent years, life expectancy rates have improved dramatically around the world. The ability to live longer has increased significantly because of better health care, available information, medication, exercising routines, medical devices, and so forth. Many individuals seek to live independently as long as possible to the extent their health, mental state, and personal conditions allow. In many cases, individuals that live independently have been found to be happier and experience more fulfilled lives. Living independently as possible may be difficult for some individuals because of medication requirements, physical limitations, and other conditions for which they may need at least minimal assistance.

SUMMARY

One embodiment provides a system, method, device and computer program product a system, device, and method for acquiring information. An image and metadata associated with the image are captured utilizing a wireless device. The image and the metadata are associated with a device incapable of communication with an external device. Information associated with the device and user information is determined. The user information is characterized in context of historical data for at least the user and other similar users. The information is distributed from the wireless device to one or more authorized devices.

Another embodiment provides a system, method, device, and computer program product for collecting user information. An image and metadata associated with the image are captured utilizing a wireless device. The image and the metadata are associated with a device incapable of communication with an external device. User information associated with at least the image and the metadata is automatically determined. The user information is characterized in context of historical data for at least the user and other similar users. The user information is distributed from the wireless device to one or more devices associated with the user information. A health regiment of the user is automatically adjusted in response to the user information.

Another embodiment provides a wireless device for user information collection. The device includes one or more cameras for capturing an image and metadata associated with the image. The image and the metadata are associated with a device incapable of communication with an external device. The wireless device includes one or more processors for processing the image and the metadata associated with the image. The wireless device includes one or more memories for distributing the user information from the wireless device to one or more devices associated with the user information.

Another embodiment provides one or more machine-readable media with a wireless device having stored therein instructions, which when executed by one or more processors cause the one or more processors to perform operations that capture an image and the metadata associated with the image utilizing the wireless device. The image and the metadata are associated with a device. The device is incapable or unable to communicate with the wireless device. Process the image and the metadata utilizing the wireless device to determine user information associated with the device. Distribute the user information from the wireless device to one or more devices associated with the user information.

Another embodiment provides a system, method, device, and computer program product for monitoring a status of a user. One or more biometrics associated with a user in a residence where the user resides are sensed. A status of the user is determined in response to sensing the one or more biometrics. One or more questions about the status to the user are communicated. One or more answers to the one or more questions communicated to the user are received. The status is communicated to an administrator of the residence. The status is communicated in response to one or more of the answers. The method may also be performed by a device including a processor a memory and a set of instructions executed to perform the described method.

Yet another embodiment provides a system for determining a status of a user. The system includes a number of sensors sensing one or more biometrics of a user. The system also includes a controller in communication with the number of sensors determines the status of the user in response to the one or more biometrics, communicates one or more questions about the status to the user, and receives one or more answers. The system includes a transceiver in communication with the controller that communicates the status in response to receiving the one or more answers.

BRIEF DESCRIPTION OF THE DRAWINGS

The present embodiments may be better understood, and numerous objects, features, and advantages made apparent to those skilled in the art by referencing the accompanying drawings.

FIG. 6 is a flowchart of a process for delivering medication in accordance with an illustrative embodiment;

FIG. 7 is a flowchart of a process for dispensing medication in accordance with an illustrative embodiment;

DESCRIPTION OF EMBODIMENT(S)

Figure 1:
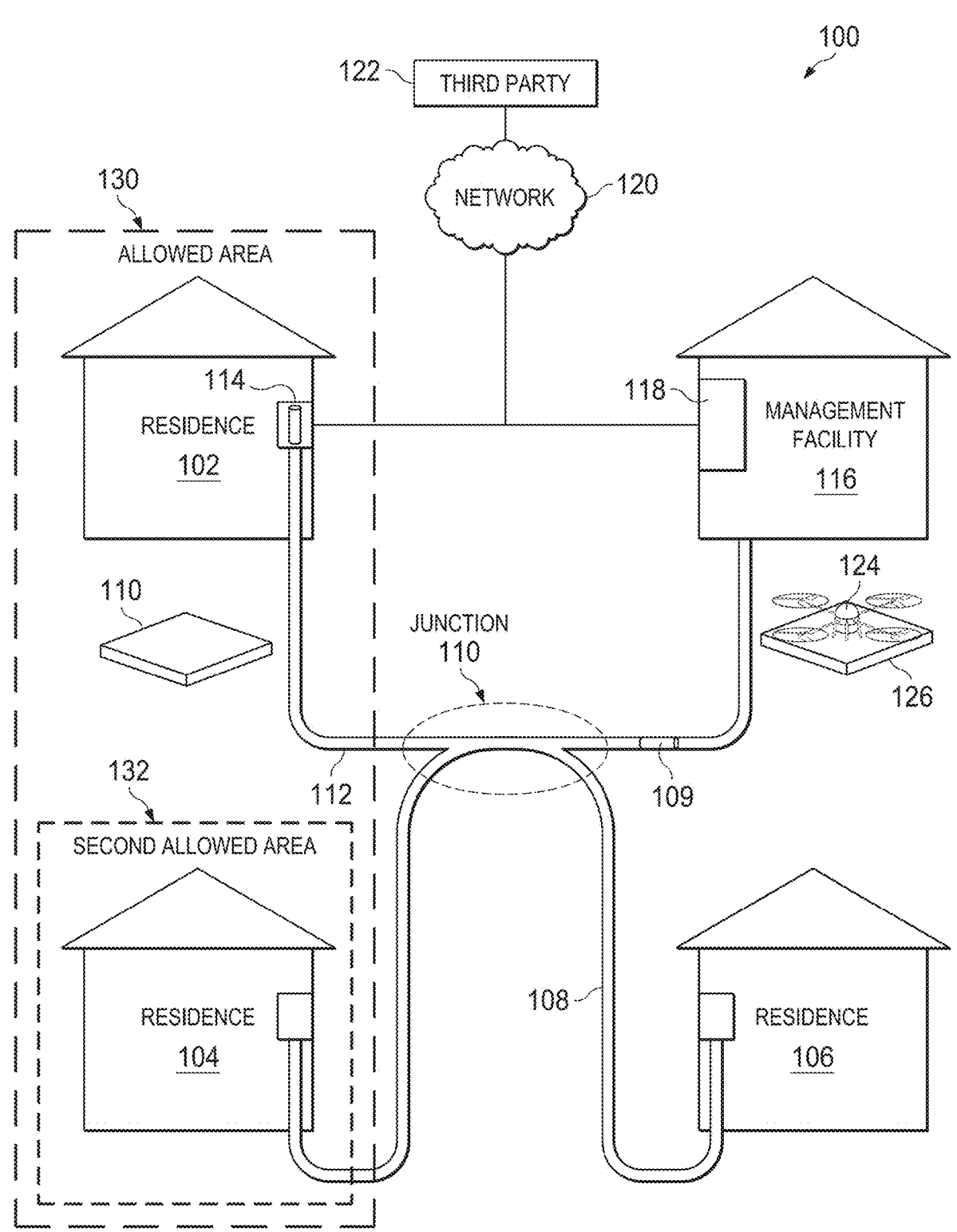
FIG. 1 is pictorial representation of a delivery and medication system in accordance with an illustrative embodiment.

The description that follows includes exemplary systems, methods, devices, techniques, instruction sequences and computer program products that embody techniques of the present inventive subject matter. However, it is understood that the described embodiments may be practiced without these specific details. In other instances, well-known instruction instances, protocols, structures, components, and techniques have not been shown in detail in order not to obfuscate the description. The illustrative embodiments are meant to be combined across Figures, claims, and embodiments regardless of natural or artificial restrictions or limitations imposed upon the content. The description and language herein, is applicable across all of the Figures. The users of the illustrative embodiments may be referred to as users, patients, individuals, or so forth.

The illustrative embodiments provide a method, system, and apparatus for the capture of biometric data from any source using scanning, optical data extraction, metadata enhancement, and outcomes analysis. One embodiment provides a healthcare monitoring system including biometric testing, data extraction, analysis, processing, display, and archiving for health-related data. A user may be identified (e.g., authenticated and authorized) to upload, receive, and communicate applicable data. The data may be communicated over secured network systems including mobile Internet networks.

The illustrative embodiments may utilize any wireless communication or computing device equipped with a camera to capture and send data through an automated process. One or more software applications executed by the communications or computing devices may be utilized to send and receive data (e.g., through a user interface presented on a touch screen). The illustrative processes may be simplified and automated. The illustrative embodiments automate the capture, recognition, and mapping of user-facing communications, displays, panels, controllers, touch screens, and available content. The content may be captured for computing, communications, fitness, health, or other systems, devices, equipment, instruments, or components, such as scales, thermometers, glucometers, spirometers, pulse oximeters, blood pressure devices, exercise equipment, and so forth regardless of whether they are digital or analog devices. The illustrative embodiments may generate digital content directly from images captured by the end-users. The illustrative embodiments may utilize machine face recognition technology, optical character recognition, and other machine vision systems to capture data, visual, and information. In one embodiment, the data may be captured from a device that is incapable, incompatible, or unable to communicate with the image capture device (e.g., wireless device, computing device, etc.). For example, the device may be a dumb device, such as a treadmill, exercise bike, traditional analog or digital scale, blood pressure cuff, non-wireless wearable, or so forth.

The illustrative embodiments capture visual data as well as metadata, including, but not limited to, time of capture, geographic data (e.g., address, elevation, etc.), user, and so forth. The captured data is securely delivered to designated users, devices, systems, cloud networks/systems, databases, or so forth. In one embodiment, an application (e.g., Fotodigm), is installed on a smart phone and utilized to capture data and information applicable to a user. The user-specific data may also be delivered to a user's doctor, medical professional, parent, guardian, family member, friend, electronic healthcare record (EHR), dashboard, or so forth for feedback and review.

The illustrative embodiments may remove identifiers or content to comply with the Healthcare Information Privacy Protection Act (HIPPA). For example, applicable data may be deidentified and stripped of applicable information in order to comply with laws, regulations, industry practices, privacy policies, and so forth. The applicable data may also be transmitted or stored in a digital data exchange with relationships with the World Health Organization (WHO) or other third party healthcare data providers for utilization in larger historical, populated, and mapped systems. The larger data systems may utilize the associated data and metadata to enhance diagnosis, treatment, and reporting of disease, medicinal strategies, treatments, and so forth. As a result, historical data sets, trends, treatments, strategies, drug efficacy, and other applicable information may be shared. An individual user's biometric data may be compared against applicable data sets to make inferences, determinations, predict outcomes, or so forth. In one embodiment, algorithmic analysis may be performed on applicable data.

The data captured may include biometric data, such as exercise data for cycling, running, jogging, walking swimming, hiking, weightlifting, and sports through the use of a scan or reading of the workout summary or statistics displayed. The digital or analog displays associated with smart watches, smart bands, step counters, exercise equipment, and/or biometric sensors may be captured utilizing a camera. The applicable image may be processed (e.g., OCR, etc.) to determine applicable data and metadata. The processed data may be utilized to display information to the user or communicated to secure systems and databases for utilization (e.g., deidentified to comply with HIPPA for further analysis). As a result, the illustrative embodiments allow information and data from any device to be captured for processing. Biometric measurements and monitoring performed by the illustrative embodiments may include body weight/BMI, body temperature, height, waist size, blood pressure, heart rate, oxygenation, ECG, pulse-oximetry, blood glucose/insulin levels, drug/chemical levels, respiration, and so forth. For example, images, metadata, data, and information may be captured from any number of digital or analog devices including scales, thermometers, measuring devices, scanners, tapes, blood monitors, implants (external or internal), monitors, medical devices, smart clothing/fabrics, smart glass, network gym equipment, wearables, hearables, $3^{rd}$ party applications, physical therapy systems, sleep monitors, digital displays, neural sensors, neural networks, food related data, barcodes (e.g., QR, serial number, retail, medical, point of purchase codes, etc.), The illustrative embodiments may be utilized for health monitoring, risk assessment, outcome optimization, and so forth. The illustrative embodiments reduce costs associated with previous systems by providing a simple to use process that works with legacy or non-smart devices, systems, and equipment. For example, many telehealth systems vary from $60-250 USD per patient per month. The illustrative embodiments may be less than $5-25 per patient per month. The illustrative embodiments allow dynamic information and data to be captured from any number of dumb, analog, wired, or wireless devices that may not provide the tools, information, and processing that the user or associated guardians, medical professionals, or other interested parties may need.

The illustrative embodiments also provide a distribution and monitoring system, method, and devices. A user as referred to herein may refer to a patient, resident of a facility, or other individual. A residence as referred to herein may refer to a home, apartment, assisted living facility, medical facility, commercial facility, or other location in which the user may permanently or temporarily reside or be located.

In one embodiment, the distribution system is utilized to distribute medication to one or more users. The medication may be delivered utilizing a predetermined schedule, in real-time, or based on a need or other manual selection. For example, the distribution system may be part of an assisted living facility that delivers medication for individual users or residents at meals based on their individual medical needs. The medications may include one or more different types, dosages, categories, or delivery types. The various embodiments may also provide tracking and verification information to ensure that the user received and/or utilized the medication. The facility may be a single facility or building or may be a distributed facility for delivering the medication.

The systems may include scanning equipment, monitoring devices, sensor, and other systems for determining the status of the user. For example, a wearable glucose monitor may be utilized to determine whether insulin or other medications are required for a diabetic user. Likewise, cameras, infrared scanners, or so forth, may be utilized to determine the location, pulse, and physical orientation of the user to determine whether medication or medical assistance are required. Integrated sensors may be configured to detect particular odors. For example, rotting food, mold, bodily fluids or waste, or other smells indicative of a potential problem may be sensed and reported. Thresholds may be utilized for the sensing equipment to ensure that alerts or reporting are not performed unnecessarily. As a result, medications may be delivered as needed. Real-time medication delivery may allow users to have improved circumstances and health.

In one embodiment, the medication is distributed from a central facility, such as a dispensary, pharmacy, administration office, or so forth. The distribution system may be automatic, or may be configured to interact with one or more administrators or medical professionals. In some embodiments, a central facility may serve multiple users to ensure that their medical and monitoring needs are met. In another embodiment, the administrator/caregiver and the user may have a one-to-one relationship. The medications and other items are distributed in accordance with country, state, county, and local laws and regulations for medication, medication delivery, and medical practitioners (e.g., doctors, pharmacists, nurse practitioners, etc.).

The medications may be delivered utilizing any number of delivery methods. In one embodiment, the delivery system includes a pneumatic tube network that is utilized to pneumatically drive containers to a location of the user for delivering medication. In another embodiment, one or more drones (flying or land based) may be utilized to deliver the medications. The delivery system may include a receiving point, dock, or other location configured to receive the medication associated with a user. In one embodiment, a lockbox is configured to receive containers that store the medication. The lockbox and the containers may individually or collectively include authentication systems for ensuring that the user receives the medication rather than another individual or party. For example, passwords, pins, biometrics (e.g., voice recognition, DNA, fingerprints, eye scans, etc.), may be utilized to authenticate the user.

As previously noted, monitoring equipment within the location, facility, or residence of the user may be utilized to perform monitoring. Monitoring may be performed by a medical professional, administrator, authorized observer, or family member or friend that is granted access. FIG. 1 is pictorial representation of a delivery and medication system 100 in accordance with an illustrative embodiment. In one embodiment, the system 100 may include residences 102, 104, 106, a pneumatic system 108, a junction 110, a path 112, a lock box 114, a management facility 116, a computing system 118, a network 120, a third party 122, a drone 124, landing pads 126, 128, and allowed areas 130, 132.

The system 100 may represent any number of residences, facilities, or locations in which one or more users may reside or spend a significant amount of time whether permanently or temporarily. The management facility 116 is a location within which an administrator works, lives, or is temporarily located. For example, an administrator within the management facility 116 may serve multiple users within the residences 102, 104, 106. Users within the residences 102, 104, 106, may live there alone, as family unit, with a caregiver, or in other cases as circumstances require.

In one embodiment, the management facility 116 manages the care of the residences 102, 104, 106, including, for example, building maintenance, medication delivery, and status monitoring of the users. The computing system 118 may be utilized to automatically, semi automatically, or manually control the components of the system 100. For example, the computing system 118 may receive multiple feeds, sensor inputs, data, or other information for each of the residences 102, 104, and 106 as is further shown and FIG. 3. The computing system 118 may include one or more servers, databases, routers, switches, personal computers, mobiles devices, intelligent network devices, or so forth.

In one embodiment, the computing system 118 communicates with the other portions of the system 100 through the network 120. The communications within the delivery and medication system 100 may occur on any number of networks which may include wireless networks, data or packet networks, cable networks, satellite networks, private networks, alternative networks, and publicly switched telephone networks (PSTN). The network 120 represents the different types of communication network types and configurations. In particular, the network 120 may be utilized by the different portions of the system 100 to communicate with one or more cloud, social, or medical networks or software systems. The features of the illustrative embodiments may be implemented by one or more elements of the delivery and medication system 100 independently or as a networked implementation.

The communications environment 100 may further include any number of hardware and software elements that may not be shown in the example of FIG. 1. For example, the communications environment 100 may include fiber optic cables, coaxial cables, twisted pair wires, exchanges, switches, antennas, towers, switching centers, routers, application servers, media servers, media converters, service brokers, call agents, edge routers, gateways (signaling, trunking, access, sub, etc.), IP network service providers, adapters, exchanges, switches, users, and networks.

In one embodiment, the computing system 118 may include a specialized program, algorithm, or set of instructions that are executed by one or more processors to implement the systems and methods herein described. For example, the computing system 118 may act as a controller for the other portions of the system 100.

In one embodiment, the residences 102, 104, 106 are connected by the pneumatic system 108. The pneumatic system may also be referred to as a pneumatic tube transport (PTT) for moving cylindrical or round containers through a network of tubes by compressed air or by partial vacuum. The pneumatic system 108 may move one or more containers 109 through the pneumatic system 108 individually, concurrently, or simultaneously. In one embodiment, the pneumatic system 108 represents a number of tubes formed from plastic, glass, metal, wood, polymers, or so forth. The tubes of the pneumatic system 108 may take any number of shapes or paths, such as direct, free form, or grid-like.

The container 109 is configured to be communicated or move from the management facility 116 to any of the residences 102, 104, 106. The container 109 may be formed of a low resistance material or include bearings, wheels, or slides to encourage free motion within the pneumatic system 108. The pneumatic system 108 may include one or more junctions, such as junction 110. The junction 110 may be controlled by the computing system 118 to route the container 109 within the pneumatic system 108. For example, the junction 110 may include any number of actuators, ramps, doors, diverters, arms, or so forth that select one of the pathways of the pneumatic system 108 for routing the container 109. In one embodiment, the pneumatic system 108 includes smart connections, such as a connected network controller for each segment of the pneumatic system or for the junction 110 for controlling and tracking motion of the container 109 within the pneumatic system 108. For example, one or more buses or wires may be integrated with or connected to the tubes of the pneumatic system 108 to control components, such as the junction 110. The container 109 may be driven within the pneumatic system 108 utilizing compressed gases and/or suction generated by one or more pumps integrated with or connected to the system. Sensor within the pneumatic system 108 may also be utilized to detect the location of the container 109 and to control various components, such as the junction 110.

The pneumatic system 108 may have separate tube paths that terminate at each of the residences 102, 104, 106 and management facility 116. In one embodiment, the various tubes in of the pneumatic system 108 may terminate at a lockbox, such as the lockbox 114. Each of the residences 102, 104, 106, and the management facility 116 may include a lockbox 114, dock, or so forth. The lockbox 114 may be utilized to securely receive the container 109. For example, the lockbox 114 may be configured to receive one or more containers simultaneously, and to store the containers for delivery at the specified time. The lockbox 114 may include one or more locking mechanisms that are interconnected with an authentication system. The lockbox 114 may receive an identifier or authentication information to ensure that the medication is delivered to the user for consumption (and not to another party that may live at the applicable residence or that may be visiting). For example, a passcode, pin, voice identifier, or biometric identification may be utilized to release medication within the lockbox 114 and container 109 to the user. In another example, an administrator in the management facility 116 may send a command to the lockbox 114 to release the container 109 and/or medication to the user based on audible, visual, or other authentication.

In another embodiment, one or more of the residences 102, 104, 106 may include the landing pad 126. The landing pads 126, 128 are configured to receive the drone 124. For example, medications may be loaded onto the container 109 that is then attached to the drone 124. The drone 124 may then fly or drive to the landing pad 128 from the landing pad 126. In one embodiment, the drone 124 may travel to the location of the landing pad 128 and deliver the container 109, after which the drone returns back to the landing pad or 126 to be loaded, charged, maintained, or prepared for the next delivery. For example, the drone 124 may be preprogrammed with a route to reach the pad 110 of the residence 102. In another embodiment, the drone 124 may remain at the residence 102 until the container 109 is retrieved from the drone 124 or until subsequently needed. The drone 124 may leave the container 109 on the landing pad 128. The drone 124 may alternatively dock with the lockbox 114 to deliver the medication for the user of the residence 102. The medications may be delivered in a stand-alone form that is easily consumed, injected, or otherwise applied or within a small container as is herein described.

In one embodiment, the route or delivery path, including speed, direction, altitude, and distance between the landing pad 126 and the landing that 128 may be pre-programmed or loaded into the drone 124 or wirelessly communicated from the computing system 118 to the drone 124. In another embodiment, the landing pad 126, 128, lockbox 114, or the residence 102 may include a signal or beacon that is utilized to signal a location to the drone 124. The drone 124 may include one or more camera systems, sensors, or so forth for navigating the residences 102, 104, 106, the, power lines, trees, or other obstacles within the environment represented by the system 100. As a result, the drone 124 may determine a travel path in real-time. In one embodiment, the landing pad 126 may be retracted from the management facility 116 (or the residences 102, 104, 106) in order to allow an administrator or user to prepare the drone 124 and the corresponding container 109. In addition, the drone 124 may be accessed from within the residence 102 utilizing a retractable pad regardless of the weather or other conditions. In another embodiment, the drone 124 may be configured to utilize pre-programmed flight or drive information as well as real-time sensing to avoid new or temporary obstacles (e.g., delivery trucks, power lines, birds, people, etc.). The computing system 118 may communicate the routes to the drone 124 utilizing a wired or wireless connection for storage in the memory or navigation system of the drone 124. In another embodiment, a robotic system or kiosk of the management facility 116 may be utilized to load and unload the medicine or other payload carried by the drone 124.

In one embodiment, the system 100 may also be configured to track users. The tracking may be performed based on their own consent, consent of a guardian/custodian, court order, or so forth. In one embodiment, the allowed area 130 is a range, perimeter, or area associated with the residence 102 and the corresponding user. For example, the allowed area 130 may specify areas that the user is allowed to be while areas outside the allowed area 130 may be disallowed. The user may wear a location device (e.g., GPS tracker, Apple watch, Android wear, smart jewelry or clothing, etc.) that indicates the location and physical orientation of the user at any time. In another embodiment, a number of cameras within the system 100 may be utilized to determine the location of the user without violating the user's privacy. As a result, the user may be able to move anywhere within the allowed area 130 without an alert or alarm being generated. If the user associated with the residence 102 is outside the allowed area 130, an alert or alarm may be generated. The alarm may be generated for an administrator within the management facility 116. In another embodiment, the alert is for a third party, such as a friend or family member of the user. Any number of criteria, user preferences, or parameters may be utilized to determine who, how, and when alerts or alarms are generated.

In one embodiment, the allowed area 130 may be dynamically reconfigured based on privileges, time of day, days of the week, or so forth. For example, the allowed area 130 may be automatically expanded to cover a recreation area near the management facility 116 based on a request from a user or on specified days. The user may make requests through one or more applications or programs available to the user that are tracked by the system 100. The allowed area 130 may also be beneficial for users that are experiencing memory issues. For example, an alert may be given to the user prompting him to return to the allowed area 130. In one embodiment, the alert is given through a smart devices, such as cell phone, anklet, necklace, smart watch (e.g., Apple watch, Samsung watch, speaker, etc.), or other smart wearable product issued to the user.

As shown, the second allowed area 132 may be associated with a user of the residence 104. The size, shape, and other information associated with the allowed area 130, 132 may vary based on the individual circumstances of the users of the residences 102, 104. For example, the allowed area 130 may include both the residence 102 and the residence 104. However, the allowed area 132 may only include the residence 104.

Figure 2:
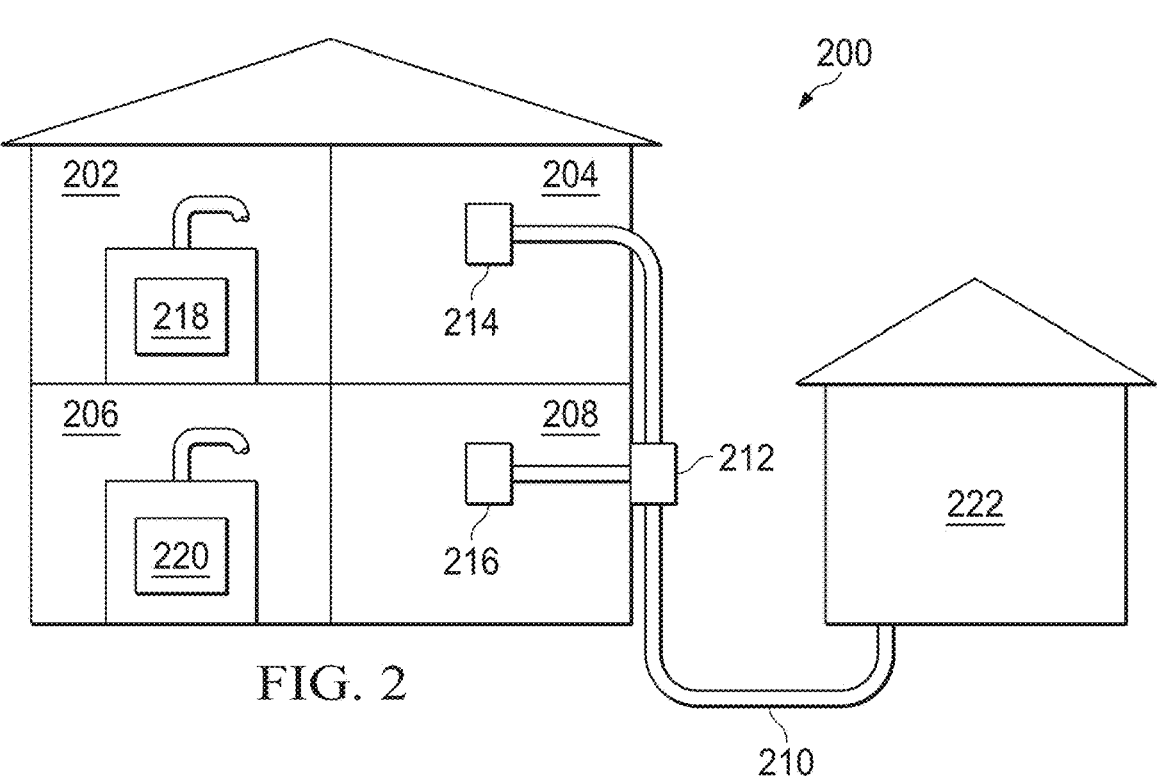
FIG. 2 is a pictorial representation of another delivery and medication system in accordance with an illustrative embodiment.

FIG. 2 is a pictorial representation of another delivery system 200 in accordance with an illustrative embodiment. In one embodiment, the system 200 may include a facility 201, residences 202, 204, 206, 208, a pneumatic system 210, a junction 212, lockboxes 214, 216,218, 220, and a dispensary 222. As shown, all or portions of the system 200 represent or may be integrated with the system 100 of FIG. 1.

As shown, the delivery system 200 may be utilized for single occupancy residences, multiple occupancy residences, and so forth. In one embodiment, the facility 201 may be a multi-level residence facility. For example, individual users or groups of users may live in each residence 202, 204, 206, 208. As shown, the residences 202 and 206 include a first type of lock box 218, 220 and the residences 204, 208 include a second type of lockbox 214, 216.

As previously described, the lockboxes 214, 216 are interconnected with the pneumatic system 210. The lockboxes 214 and 216 receive one or more containers through the pneumatic system 210. As previously noted, the junction 212 routes the containers to the lockboxes 214, 216, respectively. In another embodiment, the pneumatic system 210 may also be interconnected to the lockboxes 218, 220.

As shown, the lockboxes 218, 220 may be integrated with furniture or a fixture, such as a kitchen sink, desk, drawers, or cabinets. The lockboxes 218, 220 may be stocked by a delivery person or device. The delivery person may access the lockboxes 218, 220 from inside the residence 202, 206, or from the outside thereof. For example, the lockboxes 218, 220 may have an access door or port that is available from a hallway, secured room, garage, exterior wall, or other location for the delivery person to access the lockboxes 218, 222 to deliver medications, or other sensitive items. For example, the lockboxes 218, 220 may be utilized to deliver sensitive documents or authorization information for the users. The lockboxes 218, 220 allow the user to more easily access the medications. The lockboxes 218 are secure containers. The lockboxes 218, 220 may include one or more doors for access by both a delivery person and a user. For example, a key lock on a first door of the lock box 218 may open into a utility closet for access by a delivery person and a biometric lock (e.g., fingerprint, voice, etc.) on a second door of the lock box 218 may open into the residence 202 for access by a user as needed. The lockboxes 218, 220 may include the secured doors (and hinges) and may be sealed against outside influences (e.g., moisture, fire, poor air conditioning, heat, etc.).

In one embodiment, the lockboxes 214, 216, 218, 220 are voice controlled. For example, the user may request "Please give me my medicine." Once the user's voice is recognized or another authentication is verified, one or more of the lockboxes, 214, 216, 218, 220 may open to deliver the medication or other secured item. As previously disclosed, a pin, passcode, fingerprint or other information may also be utilized. In one embodiment, a radio frequency identifier (RFID) chip, near field communication (NFC) transceiver, or other similar component carried by, worn, or injected in the user may be utilized to authenticate the user.

Figure 3:
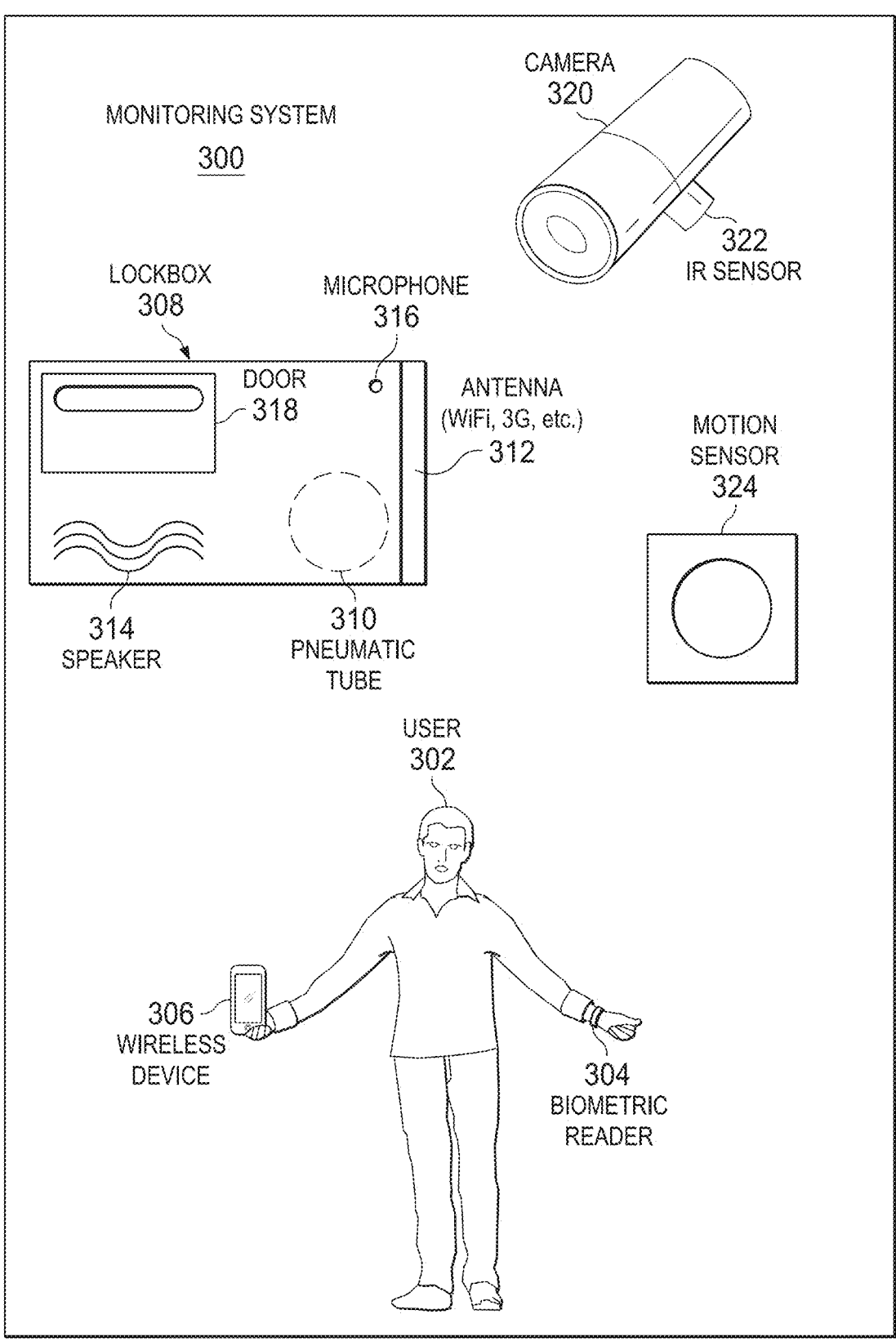
FIG. 3 is a pictorial representation of a monitoring system in accordance with an illustrative embodiment.

FIG. 3 is a pictorial representation of a monitoring system 300 in accordance with an illustrative embodiment. The monitoring system 300 may include any number of devices or components as illustrated in the systems 100 and 200 of FIGS. 1 and 2. In one embodiment, the monitoring system 300 may include a user 302, a biometric reader 304, a wireless device 306, a lockbox 308, a pneumatic tube 310, an antenna 312, a speaker 314, a microphone 316, a door 318, a camera 320 an infrared (IR) scanner 322, and a motion sensor 324.

In one embodiment, the lockbox 308 may be electrically powered. For example, the lockbox 308 may be connected to the wiring of the residence. In another embodiment, the lockbox 308 may include batteries for powering the lockbox 308 as a stand-alone device. The batteries may power the lockbox 308 even when there are power outages, intermittent power, or other potential issues. The door 318 is configured to open the lockbox 308 to access one or more containers, medications, or other items within. In one embodiment, the door 318 may only be opened by entering a combination, code, password, a number, biometric, or so forth. As a result, the lockbox 308 may include one or more keyboards, combinations, or so forth. In another embodiment, the lockbox 308 may include another door or port (not shown) on the backside or side of the lockbox 308 for another party to access or fill the lockbox 308 as is described herein.

In one embodiment, the lockbox 308 alerts the user 302 when a container has been delivered to the lockbox 308. The lockbox 308 may include any number of indicators, such as LEDs, touchscreens, or so forth, that display information, data, or alerts to the user 302. For example, the indicators may indicate when the lockbox 308 is full or has received content, when empty, or other potential issues. The door 318 may also include a window or peephole (not shown) for the user to determine whether one or more containers are within the lockbox 308. The window may be utilized to determine whether the container needs to be retrieved or returned to the dispensary.

The speaker 314 may be configured to play audio information to the user 302. For example, through the speaker 314, the user 302 may receive instructions to remove the container within the lockbox 308 and to take the associated medication. The speaker 314 may also be utilized to provide instructions for taking the medication, such as "Please take this medication after eating a full meal and with a half glass of water." Instructions may be provided for other types of medicines, topical, injection, or so forth. The speaker 314 may be controlled through logic of the lockbox 308 controlling the operations thereof.

The microphone 316 may be utilized to receive important feedback from the user 302. For example, the user 302 may ask for assistance. In another embodiment, the user may request instructions regarding how to open the lockbox 308 or take a particular medication. The lockbox 308 may also act as an emergency beacon. For example, if the user 302 is injured or otherwise needs assistance, the user 302 may provide a request for help, keyword, or other information to receive help from either an administrator, paramedics, or other response personnel. As a result, the lockbox 308 may act as a lifeline for the user 302. The lockbox 308 may also function as an emergency router to receive alerts from a local device within the residence or location before relaying the message, communication, or alert to a central system, caretaker, administrator, number of users, or so forth. For example, an application executed by the wireless device 306 (e.g., a cell phone or wearable utilized by the user 302) may prompt the user 302 for his/her status and in response to a non-response or response indicating that there is a problem may take additional actions, such as activating the camera 324 or other sensors of the monitoring system 300. Any number of other speakers, microphones, and sensors within the system 300 may be utilized to determine relevant information, communicate with the user 302, and receive meaningful feedback. The microphone 316 may also be utilized to perform voice recognition or receive a password before the door 310 is unlocked for access by the user 302. For example, the user may be required to state his name and a pass phrase to open the door 308.

The antenna 312 may be configured to communicate with any number of other smart devices within the system 300 or environment. In one embodiment, the lockbox 308 may communicate with a computing device that controls a number of lockboxes from an administrator facility. The antenna 312 may be connected to a wireless network interface that communicates with a processor, chipset, or logic of the lockbox 308. The lockbox 308 may be connected to a hardwired communications connection or line or may utilize a wireless connection, such as Wi-Fi, cellular data, or so forth.

Lockbox 308 may be configured to communicate with one or more computing or communications devices within the residence. For example, the antenna 312 may communicate with the wireless device 306. Alerts regarding deliveries, scheduled medicine consumption, status verification, or so forth, may be sent to the wireless device 306. Likewise, the lockbox 308 may receive user input, feedback, and so forth through the wireless device 306. Additional relevant information may be communicated from the lockbox 308 to the wireless device 306. The lockbox 308 may also communicate with cellular towers and systems or remote devices, such as computer systems utilized by administrators assigned to the user 302.

Various devices within the system 300 may be configured to determine the location, orientation, and status of the user 302. In one embodiment, the location of the user 302 may be determined utilizing one or more cameras, such as the camera 320 that may be installed throughout the residence. The camera 320 may be configured to sense any number of spectrums for determining distinct information about the location and condition of the user (e.g., hyperspectral imaging, thermal, infrared, X-ray, etc.). The camera 320 may also include an electronic nose for detecting odors or flavors. The example, the camera 320 may include any number of chemosensors or gas chromatography devices for detecting odors. The odor sensing devices may include a sampling unit, sensor array, pattern recognition modules, and a computing/logic system. For example, the camera 320 may be configured to detect a number of distinct smells, such as mold, rotten food, excessive bodily waste or fluids, or so forth. These types of smells may indicate that there is a problem within the monitoring system 300 (e.g., residence, room, etc.) or that the user 302 may need assistance with various issues. For example, if the user 302 is in the first stages of Alzheimer's disease, the user 302 may still be functional enough to take care of himself, but may forget to wash the dishes which may detected by the camera 320 as a putrid odor that may communicate an alert that a caregiver needs to provide a reminder, some instructions, or assistance to the user 302 audibly through the speaker 314, visually through a connected display (e.g., wireless device, television, computer, heads up display, etc.) or in person.

The monitoring system 300 may also include one or more motion sensors 324 to determine the location of the user 302, an activity level of the user, 302 and other information associated with the user 302. This information may be saved to a database accessible to a caregiver, administrator, or the user 302. The biometric reader 304 may also be utilized to determine the location of the user 302 utilizing wireless triangulation, radio frequency imaging, signal differential, global positioning, or so forth. In one embodiment, a blue dot may be utilized on a separate computing system to represent the location of the user 302 for one or more parties authorized to view the location of the user 302.

The biometric reader 304 may be configured to measure temperature, glucose levels, blood oxygenation, blood pressure, and any number of other characteristics, parameters, or biometrics of the user 302. The biometric reader 304 may also include actuators that indicate the orientation of user 302. For example, the biometric reader 304 may indicate whether the user 302 is standing, sitting, or laying. In one embodiment, if the user 302 is determined to be laying in a position that is not associated with a bed, couch, or so forth, an alert may be generated for an authorized party. In one embodiment, the biometric reader 304 is a smart watch (e.g., Apple watch) that communicates wirelessly with the lockbox 308 through the antenna 312).

Figure 4:
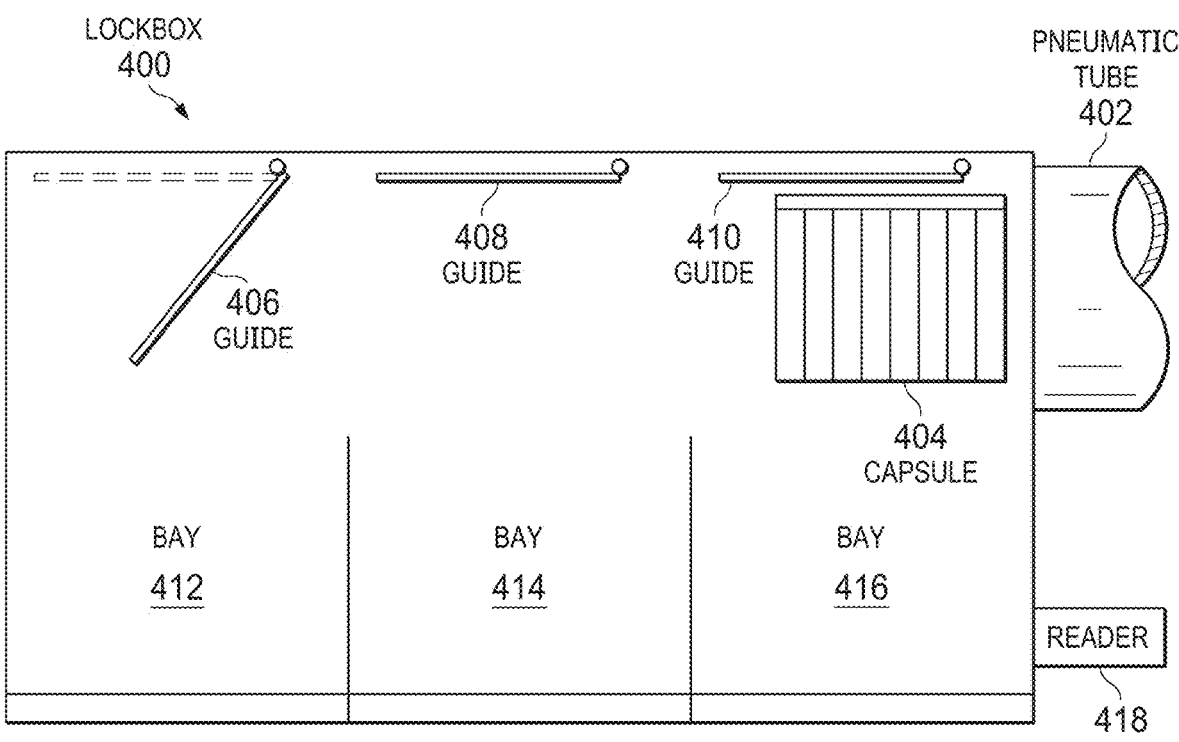
FIG. 4 is a partially cut-away top view of a lockbox 400 in accordance with an illustrative embodiment.

FIG. 4 is a partially cut-away top view of a lockbox 400 in accordance with an illustrative embodiment. The lockbox 400 may be integrated with or connected to a wall, floor, or other structure within a residence. In one embodiment, a pneumatic tube 402 may be part of a pneumatic system as is herein described. The pneumatic tube 402 may be attached to the lockbox 400 utilizing any number of couplings. A container 404 is communicated through the pneumatic tube 402 to the lockbox 400. In one embodiment, the lockbox 400 may include guides 406, 408, 410. In one embodiment, the guides 406, 408, 410 are arms that may rotate about a pivot point, flex, or otherwise move to guide the container 404 to one of the bays 412, 414, 416. For example, as shown in FIG. 4 the guide 406 may pivot to guide the container 404 to the bay 412.

The guides 406, 408, 410 may guide the container 404 into one of multiple bays 412, 414, 416. The guides 406, 408, 410 may also represent magnetic, air pressure, or other mechanical diverting systems. The lockbox 400 may include any number of bays 412, 414, 416 or different containers. For example, the lockbox 400 may include a bay for each day of the week so that medications may be easily separated based on the day of the week for the clarity of the user. In one embodiment, each of the bays 412, 414, 416 may be accessed individually by multiple doors, or collectively, utilizing a larger door. In another embodiment, the lockbox 400 may include a single guide and bay for simple operation.

The reader 418 authenticates the identity of the user. In one embodiment, the reader 418 utilizes an authentication signal, device (e.g., RFID chip, proximity to wireless device or identifier, etc.), biometric read from the user, combination, or other secure identifier. For example, the reader 418 may analyze a voice sample provided by the user, a fingerprint, retinal identification, or other user information.

Figure 5:
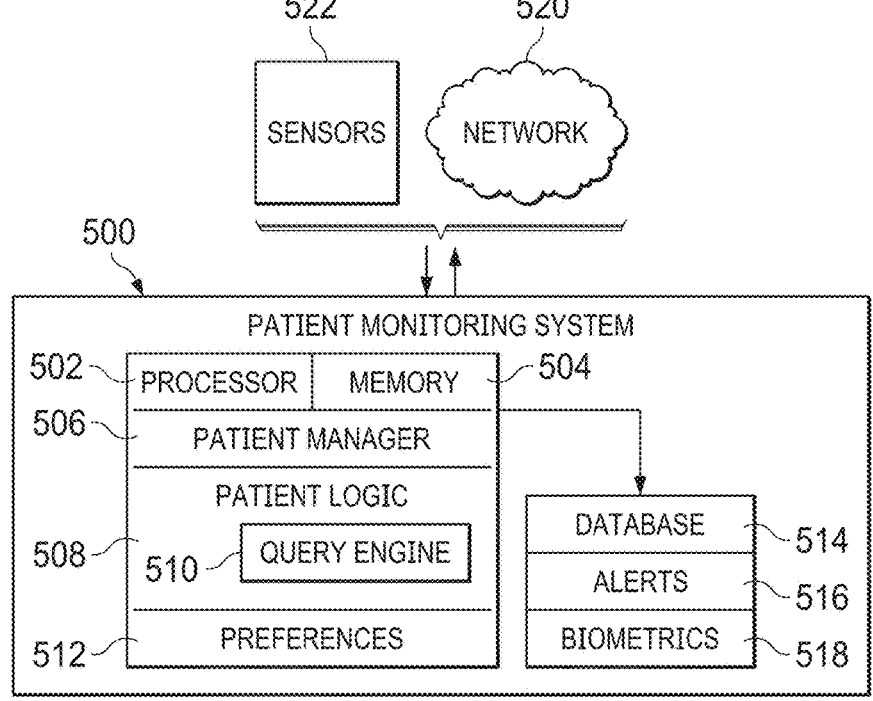
FIG. 5 is a block diagram of a patient monitoring system in accordance with an illustrative embodiment.

FIG. 5 is a block diagram of a patient monitoring system 500 in accordance with an illustrative embodiment. In one embodiment, the patient monitoring system 500 may include a processor 502, a memory 504, a patient manager 506, patient logic 508, a query engine 510, preferences 512, a database 514, alerts 516, and biometrics 518. The patient monitoring system 500 may communicate with a network 520 and sensors 522. The patient monitoring system 500 may be representative of any number of computing or communications devices. For example, the patient monitoring system 500 may be a wireless device, such as a smart phone. The smart phone may include one or more machine-readable media having stored in the memory 504 instructions, which when executed by one or more processors 502 cause the processors 502 to perform operations, functions, processes, and methods as are described herein. Various other components, modules, and units may be included in the patient monitoring system 500 that are not described for purposes of brevity. For example, the patient monitoring system 500 may include any number of processors, memory, chipsets, cards, buses, interfaces, ports, connections, storage systems, and so forth. The patient monitoring system 500 may operate autonomously, semi-autonomously, manually, or any combination thereof.

The patient monitor 506 is configured to store and manage information for a number of patients. The patient logic 508 may represent digital logic, firmware, software, or a combination thereof, for performing distribution, monitoring, and management of one or more patients. The query engine 510 may be configured to query data within the database 514, as well as other portions of the patient monitoring system 500.

The preferences 512 control parameters, criteria, and user preferences that control how the patient, distribution, monitoring, and management is performed by the systems herein described. For example, how frequently are one or more users contacted to determine their status, when are monitoring systems activated and analyzed, and how are the users monitored and cared for. The database 514 stores information and data for the patients that are associated with the patient monitoring system 500.

The alerts 516 are configured to send alerts to one or more designated parties. For example, a number of different individuals may be notified through software alert, text message, email, phone call, or other types of communication. The conditions for the alerts 516 may be specified by the preferences 512 or the alerts 516.

The biometrics 518 store biometric information for a number of users. The biometric information may be utilized to authenticate the user. The biometrics 518 may also be utilized to determine the status of a user. For example, the biometrics 518 may include thresholds for determining whether the user is within acceptable levels, such as temperature, heart rate, blood pressure, hormone levels, chemical levels and excretions, pupil dilation, response times, and so forth.

The sensors 522 may include any number of cameras/optical sensors, biometric sensors, and so forth. The sensors 522 may capture the biometrics 518 utilized to identify one or more users utilizing the patient monitoring system 500.

The biometrics 518 may also authorize various processes, actions, functions, communications, treatments, or so forth. Images of applicable devices may be captured from the patient monitoring system 500 or the sensors 522. For example, the sensors 522 may include a camera that captures an image and associated metadata for a device being utilized by a user (e.g., exercise equipment, medical device, etc.). The processor 502 may process the image and the metadata to determine user information. The user information may specify information and data gathered about the health, status, physical condition, exercise abilities, or so forth for the user. The metadata may further characterize the user information (e.g., when captured, where captured, type of device, applicable activity, user, etc.).

In one embodiment, the processor 502 is circuitry or logic enabled to control execution of a set of instructions. The processor may be one or more microprocessors, digital signal processors, application-specific integrated circuits (ASIC), central processing units, or other devices suitable for controlling the patient monitoring system 500 including one or more hardware and software elements, executing software, instructions, programs, and applications, converting and processing signals and information, and performing other related tasks. The processor may be a single chip or integrated with other computing or communications components of the illustrative systems.

The memory 504 is a hardware component, device, or recording media configured to store data and information for subsequent retrieval or access at a later time. The memory 504 may be or include static and/or dynamic memory. The memory 504 may include one or more of a hard disk, random access memory, cache, removable media drive, mass storage, or configuration suitable as storage for data, instructions, and information. In one embodiment, the memory 504 and the processor 502 may be integrated. The memory 504 may use any type of volatile or non-volatile storage techniques and mediums. The memory 504 may store information and related to the scanned or captured devices, user, system, biometrics, identification/authorization, medical conditions, treatments, and other peripherals, such as a wireless device, wearable devices, hearable devices, and so forth. In one embodiment, the memory 504 may display instructions or programs for controlling a user interface including one or more touch screens, LEDs or other light emitting components, speakers, tactile generators (e.g., vibrator), and so forth. The memory 504 may also store the user input information associated with each command. The memory 504 may also store instructions including settings, user profiles, or user preferences for implementing communications (e.g., text, email, in-application messages, phone calls, packet communications, video, audio, augmented reality, virtual reality, or a combination thereof).

The patient monitoring system 500 may further include a transceiver (not shown) or transmitter(s) and receiver(s). The transceiver is a component comprising both a transmitter and receiver which may be combined and share common circuitry on a single housing. The transceiver may communicate utilizing Bluetooth, Wi-Fi, ZigBee, Ant+, near field communications, rear-field magnetic induction (NFMI), wireless USB, infrared, mobile body area networks, ultra-wideband communications, cellular (e.g., 3G, 4G, 5G, PCS, GSM, etc.) or other suitable radio frequency standards, networks, protocols, or communications. The transceiver may also be a dual or hybrid transceiver that supports a number of different communications. For example, the transceiver may communicate with the smart watches, hearables, or other systems utilizing wired interfaces (e.g., wires, traces, etc.), NFC, or Bluetooth communications. The transceiver may distribute the user information gathered, analyzed, and otherwise processed by the processor 502.

The components of the patient monitoring system 500 may be electrically connected utilizing any number of wires, contact points, leads, busses, wireless interfaces, or so forth. In addition, the patient monitoring system 500 may include any number of computing and communications components, devices or elements which may include busses, motherboards, circuits, chips, sensors, ports, interfaces, cards, converters, adapters, connections, transceivers, displays, antennas, and other similar components.

A physical interface of the patient monitoring system 500 may include any number of pins, arms, or connectors for electrically interfacing with the contacts or other interface components of external devices or other charging or synchronization devices. For example, the physical interface may be a micro USB port. A user interface may represent a hardware and software interface for receiving commands, instructions, or input through the touch (haptics) of the user, voice commands, gesture, or predefined motions. The user interface may be utilized to control the other functions of the patient monitoring system 500. Although not shown, one or more speakers of the user interface may include multiple speaker components (e.g., signal generators, amplifiers, drivers, and other circuitry) configured to generate sounds waves at distinct frequency ranges (e.g., bass, woofer, tweeter, midrange, etc.).

The user interface may include an LED array, one or more touch sensitive buttons or screens, portions or sensors, a screen or display, or other input/output components. The user interface may be controlled by the user or based on commands received directly from the user or a linked wireless device. The user interface may also include traditional software interfaces, such as a graphical user interface or applications that may be executed by the processor 502 for communication by the user interface FIG. 6 is a flowchart of a process for delivering medication in accordance with an illustrative embodiment. The process of FIG. 6 may be implemented by one or delivery systems or devices. The systems or devices may be standalone devices or may be interconnected or networked.

The process of FIG. 6 may begin by indicating medication is necessary for a user (602). In one embodiment, prescriptions or other medications may be tracked by a system that tracks one or more users. Information regarding the medications necessary for the user may be received before delivery or at any time by the user himself/herself, family member or friend, doctor, or other medical professional.

Next, the system determines a route to a location of the user (step 604). The location may be representative of any number of temporary or permanent locations, residences, or so forth of the user. In one embodiment, the route may include commands for the system to route a shuttle or other container including medication through a pneumatic system to the location of the user. For example, a smart shuttle containing medication for a week may be routed to a lockbox in an assisted living facility of the user. In another embodiment, the route may also be driving instructions for a delivery person to drive to the location including, driving instructions, a house number, an apartment number, and so forth. In yet another embodiment, the route may be flying or driving instructions for a drone from a first location to the second location associated with the user. For example, flying instructions may include a flight path and instructions for landing on a pad, connecting to the docking system, authenticating delivery, or so forth.

Next, the system receives medication in a container for transport (step 606). The container represents any number of shuttles, vessels, or devices. For example, the container may include a smart shuttle. The shuttle may include logic for controlling distribution of the medication(s) stored within. In one embodiment, the shuttle may include multiple segments, portions, or chambers for storing medications for meals, days of the week, time periods, or so forth.

Next, the system sends the container through the determined route to the location of the user (step 608). For example, the container may be sent through a delivery system (e.g., pneumatic tubes, air drone, land drone, etc.) or route. The container may be sent to a holding container or lockbox to secure delivery at the location. Any number of alerts, confirmations, or alarms may be played to the user in response to the container being received. Confirmations may also be sent indicating that the container has arrived at the selected destination.

FIG. 7 is a flowchart of a process for dispensing medication in accordance with an illustrative embodiment. In one embodiment, the process of FIG. 7 may begin by receiving a medication at a designated time (step 702). As previously noted, the medication may be received through any number of delivery systems, mechanisms, or devices. In one embodiment, the medication may be communicated as needed (e.g., in real-time). In another embodiment, the medication may be delivered by day, time period, meal, or so forth. The medication may be delivered or made available by a lockbox or a shuttle temporarily storing the medication.

Next, the system indicates that the medication is available for a user (step 704). Any number of alerts, indicators, information, or messages may be communicated to the user during step 704. The indications provided by the system may be communicated audibly, visually, tactilely, or utilizing a combination of sensory systems. In one embodiment, a custom message pre-recorded by the user (or a family member, friend, doctor, or associated medical professional) may be played to the user. For example, the adult child of a user may provide instructions for the user (an elderly parent) to take medicine with lunch. The indications provided during step 704 may also be communicated to external systems or devices, such as monitoring systems, mobile devices, televisions, media devices, or so forth. The indication may be given once the medication is received or at the time the medication is to be taken by the user.

Next, the system authenticates the user is authorized to receive the medication (step 706). Authentication may be performed utilizing any number of methodologies. In various illustrative embodiments, the user may be prompted to provide one or more biometrics, pin numbers, passwords, identifiers, or so forth. The authentication may also be performed based on a tag, chip, or other identifying device associated with the user. For example, the user may be prompted to provide a voice authentication and fingerprint in order to authorize the release or complete delivery of the medication. In one embodiment, authentication of the user may be performed by a third party. For example, a video camera may be utilized to authenticate that the user is the party retrieving the information and not an unauthorized party.

Next, the system determines whether the user is authenticated (step 708). The system may provide the user a preset number of times to perform the authentication in step 706. As a result, the user is not automatically prevented from receiving the medicine in response to incorrect memory or momentary lapses. If the user is not authenticated during step 708, the system sends an alert (step 710). The alert may be sent to any number of designated parties including, but not limited to, the user, administrator, a doctor, a caregiver, family members, friends, medical professionals, or so forth. The alert 710 may specify why the authentication failed, what types of medications were being retrieved, and other information. The alert provides for additional security and may be utilized to deter unauthorized access or inappropriate use of the system.

In response to determining that the user is authenticated during step 708, the system releases safeguards to dispense the medication (step 712). The safeguards may include one or more lock, or securing mechanisms that may secure the medication. For example, the associated lockbox, shuttle chamber, or so forth, may be opened delivering the medication to the user. During step 712, the system may also provide instructions to the user for taking the medication. For example, the instructions may include information regarding whether the medication is to be ingested (time period), applied to the skin or other tissue, taken as part of a meal, taken with water, or other applicable information. In one embodiment, a camera or tracking system integrated within the lockbox or residence may be utilized to ensure that the medications are taken properly.

Figure 8:
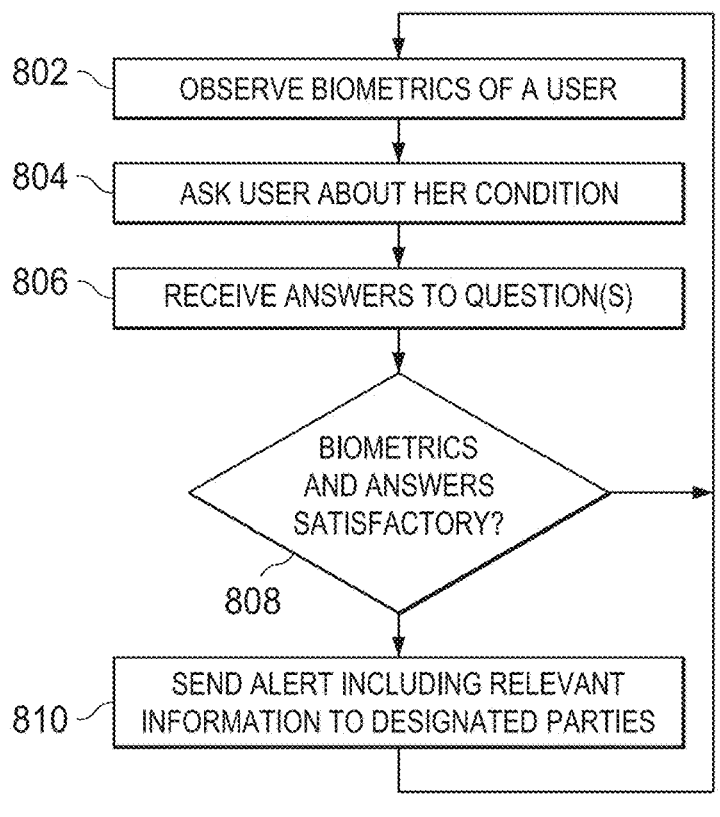
FIG. 8 is a flowchart of a process for monitoring a user in accordance with an illustrative embodiment.

FIG. 8 is a flowchart of a process for monitoring a user in accordance with an illustrative embodiment. The process of FIG. 8 may be implemented by a monitoring system. The process may begin by observing biometrics of a user (step 802). The user may represent a resident of a facility, patient, or other similar individual. The biometrics may include heart rate, pupil dilation, temperature, movements, facial expressions, blood analysis, breathing, odor, hormone levels, chemical excretions, position within an area (e.g., sitting, prone, kneeling, etc.), and so forth.

Next, the system asks the user about her condition (step 804). In one embodiment, the questions asked of the user may be played through one or more speakers, televisions, or so forth associated with the location of the user. The questions may be posed audibly, textually, electronically, or utilizing any number of other methods utilized by the user for communications (e.g., braille). The questions may also be posed utilizing a mobile device associated with the user, such as a smart phone or watch. The questions posed to the user may be preprogrammed by a medical professional, such as a doctor of the user. The questions may have any number of conditions, including time of day, biometric association, position, or so forth. For example, if the user is lying down in a position that is not associated with a couch or bed, the system may automatically ask the user if she is okay. In another example, a question may be posed in response to an elevated or low heart rate of the user to ensure that a medical event is not occurring. In yet another example, a number of questions may be posed throughout the day during specified time periods, such as meals, to check the status and well-being of the user. As is subsequently described, negative response or non-responses may be reported to one or more caregivers, administrators, family members, or other designated parties.

Next, the system receives answers to the questions (step 806). The answers relate to the questions posed during step 804. The answers may be received through one or more microphones directly or indirectly communicating with the system. For example, microphones within a bedroom may receive the answers. Alternatively, the microphone of a mobile device worn or carried by the user may be configured to receive answers and other input from the user. The answer may also be the lack of a response or a non-response that may be indicative of a potential problem. For example, the question may be posed utilizing a different system, such as an audio question instead of just a visual question presented on a wireless device or television.

Next, the system determines whether the biometrics and answers received are satisfactory (step 808). Determinations of whether the biometrics and answers are satisfactory may be determined utilizing a database, conditions, factors, or other information associated with the user or her response. For example, thresholds, or levels may be utilized to determine whether a biometric is exceeded. The answers may be analyzed to determine response time (e.g., delay in responding), speech pattern, speech cadence, words utilized during the response, and so forth. In one embodiment, the biometrics and answers throughout the day, week, and year may be archived for subsequent reference. For example, the biometric information may be utilized to determine improvements in behavior, treatment plans, condition, or so forth for the user. In another embodiment, the biometric information may be sent to a user for a decision by an administrator, medical professional, or so forth. The question and response may be sent to determine the real-time condition of the user.

If the system determines that the biometrics and answers are satisfactory during step 808, the system returns to observe biometrics of the user (step 802). If the system determines that the biometrics and answers are not satisfactory during step 808, the system sends an alert including relevant information to designated parties (step 810). The alert may be any number of messages, indicators, or other information. For example, the alert may include the biometrics, the response provided by the user, video recordings, user biometrics, audio recordings, or so forth. The designated parties may include administrators, caregivers, family, friends, or other parties designated to receive information regarding the user. As a result, the designated parties may be kept informed of the status or condition of the user even if remote from the location of the user.

Figure 9:
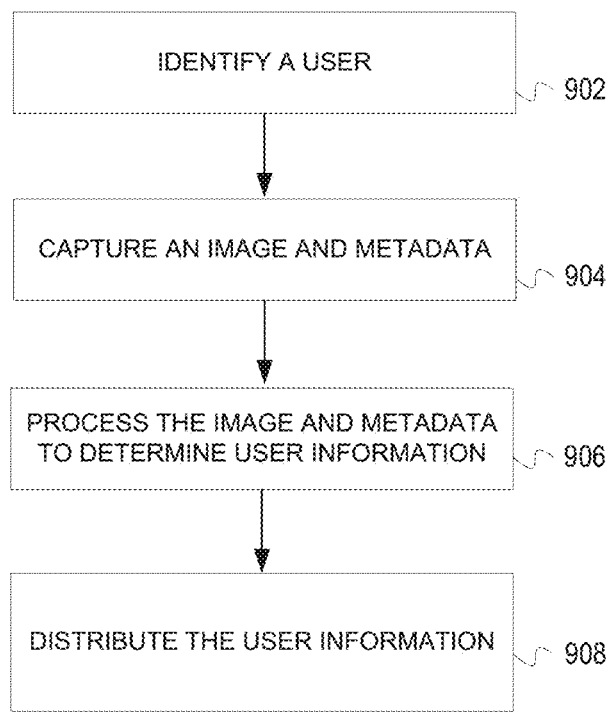
FIG. 9 is a flowchart of a process for capturing content in accordance with an illustrative embodiment.

FIG. 9 is a flowchart of a process for capturing content in accordance with an illustrative embodiment. The illustrative embodiments of FIGS. 9-11 may be implemented by any number of systems or devices as are herein described. For example, the illustrative embodiments may be implemented by a user/patient utilizing a smart phone, tablet, smart clothing, or wearable device to capture applicable data and information (e.g., exercise data and statistics, blood-pressure readings, heart rate, etc.). The process may begin by identifying a user (step 902). The user may be automatically identified based on utilization of a wireless device, user biometrics (e.g., fingerprint, facial recognition, etc.), image capture, and so forth. The user may also provide information (e.g., name, username, password, pin number, fingerprint, face, etc.) to performing identification and authentication.

Next, the system captures an image and metadata (step 904). The image may be from captured by a system or device controlled by a user, such as a smart phone, tablet, GoPro, or so forth. In one embodiment, the image may be automatically captured by the system. The image may also be manually captured by a communication, computing, visual, or camera device utilized by the user. The images may also be captured by any number of cameras or optical sensors proximate to or worn by the user (e.g., body cameras, clothing sensors, security cameras, smart glasses, smart watches, etc.). As previously noted, the image may be applicable to exercise, health monitoring, travel, ambient, lifestyle, home, or other devices, systems, equipment, or components. For example, a security system may capture an image that may be sent to the smart phone of the user. The metadata identifies applicable information associated with the image, environment, user, time period, context or so forth including, but not limited to, time/data of capture, geographic data (e.g., address, elevation, location, etc.), user, biometric data (e.g., a snapshot of the user's heart rate, respiration rate, temperature, etc.), identified device, activity, identified data/fields/information, connection status, and so forth. In one embodiment, the metadata may also identify the type of device, system, equipment, or component utilizing structure, identifiers, text permission (e.g., brand name, model number, logos, serial number, etc.), of the captured image.

Next, the system processes the image and metadata to determine user information (step 906). During step 906, various types of machine recognition, facial recognition, and optical character recognition may be performed on the image. During step 804, the system may recognize data, information, or so forth displayed or otherwise communicated by the applicable device. The system may also perform analysis and data capturing from the image and metadata.

Figure 10:
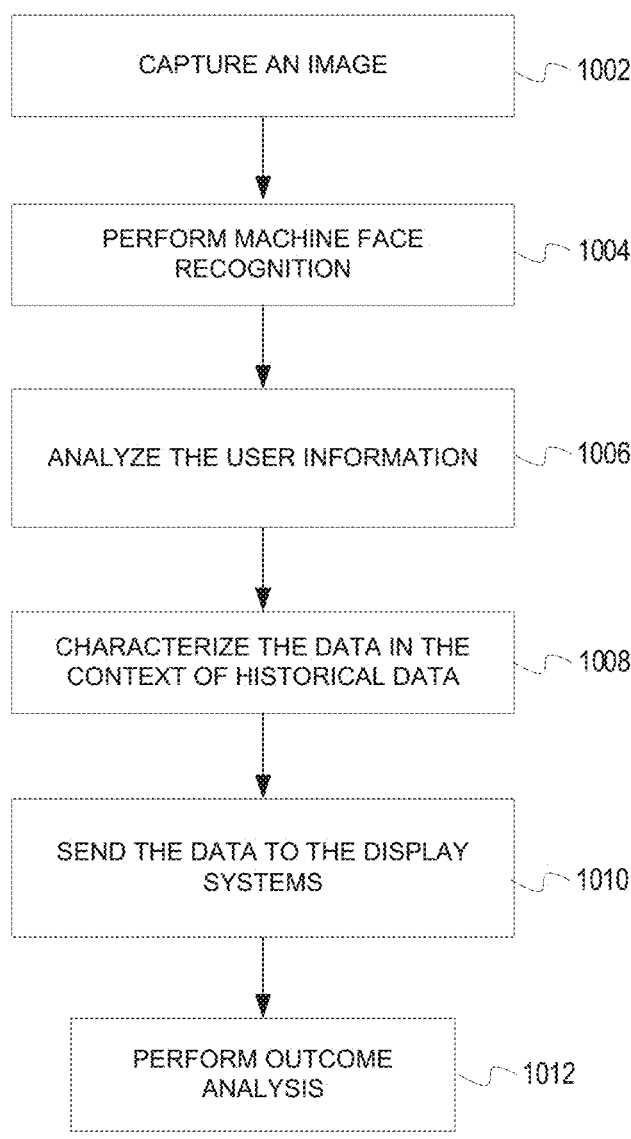
FIG. 10 is a flowchart of a process for capturing data in accordance with an illustrative embodiment.

FIG. 10 is a flowchart of a process for capturing data in accordance with an illustrative embodiment. In one embodiment, the process of FIGS. 10 and 11 may be combined with or part of the process of FIG. 9. In one embodiment, the process begins by capturing an image (step 1002). The image may be an optical image or sensory image as previously noted. The method of capturing the image may also be performed automatically or manually. During step 1002, the system may also capture applicable metadata about the user, image, environment, activity, time period, intensity, location, or so forth.

Next, the system performs machine face recognition and optical character recognition (step 1004). Machine face recognition and optical character recognition may be performed together, or as separate steps. The machine face recognition may be utilized to recognize the machine, system, equipment, or components associated with the image as well as associated metadata, data, and information. The optical character recognition may be utilized to recognize alphanumeric text, data, and information within the image. For example, optical character recognition may be utilized to read information from exercise equipment, such as average speed, pace, distance, calories, heart rate, time elapsed, time remaining, user-specified age, weight, height, ethnicity, incline/difficulty level, speed, and so forth. The system may also perform facial recognition of the user utilizing the system and capturing the image, where applicable.

Next, the system analyzes the user information (step 1006). During step 1006, the data (including the metadata) is processed to be subsequently utilized, analyzed, compared, displayed, and communicated. In one embodiment, the data may be aggregated with other user data for health monitoring and tracking. The data may also be categorized based on the user, activity, day of the week, time of day, treatment/exercise plan, goals, and so forth.

Next, the system characterizes the data in the context of historical data (step 1008). The system may utilize user data to provide historical context. The system may also use data for numerous other similar users (e.g., age, weight, condition, ethnicity, etc.). The system may also utilize all available data for numerous users and demographics.

Next, the system sends the data to the display systems (step 1010). In one embodiment, the data captured from the image may be displayed to the user in real time, near real-time, at specified intervals, daily, or as otherwise requested or specified by the user or an associated admin-istrator or medical professional. For example, the data may be displayed to a smart phone utilized to capture, analyze, and process the data.

Next, the system performs outcome analysis (step 1012). The outcome analysis may be utilized to provide specific information to the user as well as designated/interested parties, organizations, guardians, family, friends, or so forth. In one embodiment, the system may perform outcome analysis in accordance with step 1012 based on the system, method, process, and functions described in U.S. utility patent application Ser. No. 14/212,429 entitled "Platform for Optimizing Data Driven Outcomes" filed on Mar. 14, 2014 which is hereby incorporated by reference in its entirety.

In one embodiment, the illustrative embodiments may be utilized as an integrated diagnostic reporting and testing system, a data system, and a target system point-of-care testing. The data captured by the system may be processed through any number of channels, processing systems, or so forth. For example, in various channels the user/patient data may be stripped out for HIPPA compliance as well as patient privacy. In one embodiment, there may be three separate data channels utilized by the system with each channel having a different function and value.

In one embodiment, for the first channel (i.e., Channel One), the patient data is sent to a software platform (e.g., the software platform for optimizing data driven outcomes) and used as a tool for the patient and their caregiver to identify progress and increased healthy outcomes. The patient data goes into the software platform and personized healthcare regiment system whereby the patient's interactions with the system help them increase their adherence to their health regiment for the treatment of their chronic health conditions, conditions, diseases, or so forth.

In one embodiment, for the second channel (i.e., Channel Two), a data crawling system sends tests results and patient data, in a HIPPA compliant format (e.g., stripped of personal identifying data) to one or more systems (e.g., affiliates, partners, processing systems, etc.), devices, or partners. The processed test information is then received with analysis, metrics, and information regarding statistical relevance. In one embodiment, the data is dynamically captured and then added to static data repositories of individuals, partners, groups, or other associated systems. The initial data sent out may be specific to certain demographics, diseases/illnesses/conditions, In one embodiment, the initial data may be sent to government, non-government, hospital, healthcare, research, academic, or private organizations or advocacy groups, such as the National Institute for Health (NIH), Center for Disease Control (CDC), World Health Organization (WHO), Agency for Healthcare Research and Quality (AHRQ), Commonwealth Fund, European Commission (EC), Medical Research Council (MRC), U.S. Department of Defense (US DoD), Canadian Institutes of Health Research (CIHR), Howard Hughes Medical Institute (HHMI), U.S. department of Veteran Affairs, The Clinton Global Initiative, Bill and Melinda Gates foundation, Harvard, UCLA, Johns Hopkins, Stanford, Mayo Clinic, Mass General, and other similar domestic and foreign entities.

In one embodiment, for the third channel, the system data may incorporate outcome optimization software platform data (e.g., REBOOT data, etc.) designed to match outcomes of the medical regiment for the specific chronic health disease as identified for treatment of a disease based on a patient profile. The resulting enhanced data may then be sent to other organizations, groups, partners or affiliates as outlined (see for example Channel 2). The enhanced data may be matched against databases or repositories of static data before being returned to the system. The output from the third channel may provide empirical data designed to establish a road map to better health outcomes based on developed algorithms, treatment processes, treatment regiments, and so forth.

The system may communicate suggestions, treatment plans, diagnosis information, cohort/group information, medical changes, or other applicable information and data. The communicated information may be shared with the user/patient as well as associated medical professionals, guardians, family (e.g., parents, children, etc.), administrators, or so forth. For example, the user may be encouraged to make exercise, diet, medicine, treatment, and or lifestyle changes based on the outcome analysis.

The illustrative embodiments may utilize biometric sensors, memories, processing resources, and other resources of the utilized systems and devices. For example, the biometric sensors (e.g., cameras, fingerprint sensors, iris scanners, electrical contacts, etc.) may be utilized to capture information identifying the user (e.g., facial, fingerprint, bio conductivity, DNA, or other characteristics and information).

Figure 11:
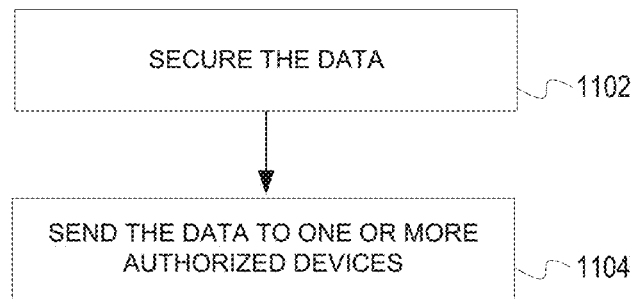
FIG. 11 is a flowchart of a process for communicating data in accordance with an illustrative embodiment.

FIG. 11 is a flowchart of a process for communicating data in accordance with an illustrative embodiment. As previously noted, the data may reference user information, metadata, analyzed/processed data, or other applicable data as is described herein. In one embodiment, the wireless device or other applicable device may secure the data (step 1102). The data may be saved locally or remotely for subsequent reference. For example, data saved in real-time may be archived for subsequent reference as historical data. The data may also be saved to any number of external devices, systems, databases, or so forth. For example, the data may be processed to remove identifying information before saving archiving the data or making the data available for additional processing. The data may also be encrypted, password protected, partitioned, or otherwise secured so that it may only be read or communicated by authorized users/ devices. In one embodiment, the data may be integrated or saved as an electronic health record. The data may also be saved in a health vault, hospital system, laboratory database, patient record, or so forth. Electronic health records may be automatically created or amended with real-time data to provide information over minutes, hours, days, months, or years.

Next, the wireless device sends the data to one or more authorized devices (step 1104). The authorized devices may also represent authorized users. The wireless device or another system, device, equipment, or component may send the data. The data may be formatted as a user file, update, message, packets, stream, or so forth. For example, the data may represent insulin levels and weekly exercise information for a user and may be sent to medical professionals and family members associated with a user. The data may have been captured from insulin monitors/testers, blood pressure devices, exercise devices (e.g., treadmills, exercise bikes, smartwatches, etc.), and so forth. The data may be distributed to provide enhanced data analysis for any number of individuals, groups, industries, companies, systems, or so forth. All applicable data may be appended as needed.

The illustrative embodiments provide efficiency (e.g., diagnosis, treatment, user actions, etc.), costs savings, research benefits, enhanced communications, outcome analysis, and numerous other benefits to individuals, organizations, and society as a whole.

Embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computer system (or other electronic device(s)) to perform a process according to embodiments, whether presently described or not, since every conceivable variation is not enumerated herein. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or another communications medium.

Computer program code for carrying out operations of the embodiments may be written in any combination of one or more programming languages, including an object-oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (for example, through the Internet using an Internet Service Provider).

Turning again to FIG. 1, in one embodiment, the computing system 118 may include a processor unit (not shown, possibly including multiple processors, multiple cores, multiple nodes, and/or implementing multi-threading, etc.). The computing system 118 includes memory. The memory may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system 118 also includes a bus (e.g., PCI, ISA, PCI-Express, HyperTransport®, Infini-Band®, NuBus, etc.), a network interface (e.g., an ATM interface, an Ethernet interface, a Frame Relay interface, SONET interface, wireless interface, etc.), and a storage device(s) (e.g., optical storage, magnetic storage, etc.). The system memory embodies functionality to implement embodiments described above. The system memory may include one or more functionalities that facilitate tracking a user, managing medication deliveries and consumption, image and metadata capture, image analysis, identification, and processing, outcome analysis, communications of related information and data, and the other illustrative embodiments. Any one of these functionalities may be partially (or entirely) implemented in hardware and/or on the processing unit. For example, the functionality may be implemented with an application specific integrated circuit, in logic implemented in the processing unit, in a co-processor on a peripheral device or card, etc. Further, realizations may include fewer or additional components not illustrated in FIG. 1 (e.g., video cards, audio cards, additional network interfaces, peripheral devices, etc.). The processor unit, the storage device(s), and the network interface are coupled to the bus. Although illustrated as being coupled to the bus, the memory may be coupled to the processor unit.

While the embodiments are described with reference to various implementations and exploitations, it will be understood that these embodiments are illustrative and that the scope of the inventive subject matter is not limited to them. In general, techniques for tracking, monitoring, and delivering medication to a user in as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the inventive subject matter. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A method for acquiring information comprising:
capturing an image and metadata associated with the image utilizing a wireless device, wherein the image and the metadata are associated with a device incapable of communication with an external device;
automatically determining information associated with the device and including user information associated with a user utilizing the device incapable of communication;
characterizing the information in context of historical data for at least the user and other similar users; and
distributing the information from the wireless device to one or more authorized devices.

2. The method of claim 1, further comprising:
identifying the user utilizing the image, the metadata, or one or more biometrics captured by the wireless device.

3. The method of claim 1, wherein the other similar users are demographically similar.

4. The method of claim 1, further comprising:
storing the information for utilization as a portion of the historical data.

5. The method of claim 4, wherein identifying information associated with the user is removed before utilizing the information as the portion of the historical data.

6. The method of claim 1, wherein the information and the user information is determined utilizing machine recognition.

7. The method of claim 1, wherein the metadata includes at least a time the image is captured and a location associated with the device.

8. The method of claim 1, further comprising:
automatically performing outcome analysis utilizing the information and the historical data associated with the information, and wherein the user is encouraged to adjust one or more of exercise, diet, and medicine based on the outcome analysis.

9. The method of claim 8, further comprising:
automatically recommending changes to a health regiment of the user in response to the outcome analysis.

10. A wireless device for user information collection, comprising:
one or more cameras configured to capture an image and metadata associated with the image, the image and the metadata are associated with a device;
one or more processors configured to automatically process the image and the metadata associated with the image to determine information and user information, and characterize the information in context of historical data for at least a user and other similar users; and
one or more transceivers configured to automatically distribute the information from the wireless device to one or more authorized devices.

11. The wireless device of claim 10, wherein the other similar users are demographically similar.

12. The wireless device of claim 10, wherein the processor further identifies the user utilizing one or more biometrics measured from the user, the image, or the metadata.

13. The wireless device of claim 10, wherein the one or more transceivers send an adjustment for a health regiment of the user in response to the information.

14. The wireless device of claim 10, wherein the one or more transceivers communicates the information to a server in communication with the wireless device, and wherein the server archives the user information for utilization as a portion of the historical data by the other similar users.

15. The wireless device of claim 10, wherein the one or more processors automatically perform outcome analysis utilizing the information, the user information, and the historical data associated with the user information, and wherein the user is encouraged to adjust one or more of exercise, diet, and medicine based on the outcome analysis.

16. The wireless device of claim 10, wherein the information is determined utilizing machine recognition.

17. The wireless device of claim 10, wherein the metadata includes at least a time the image is captured and a location associated with the device.

18. The wireless device of claim 10, wherein the one or more processors communicate with one or more biometric sensors that identify the user information.

19. The wireless device of claim 10, wherein the one or more processors automatically process the image and metadata utilizing the wireless device to determine the user information associated with the device.

20. The wireless device of claim 10, wherein the information includes exercise data, body data, or health data related to the user.

* * * * *